US007517453B2

(12) United States Patent
Bitensky et al.

(10) Patent No.: US 7,517,453 B2
(45) Date of Patent: Apr. 14, 2009

(54) MICROVASCULAR NETWORK DEVICE

(75) Inventors: Mark W Bitensky, Waban, MA (US);
Tatsuro Yoshida, West Newton, MA (US); Sergey S Shevkoplyas, Brighton, MA (US)

(73) Assignee: The Trustees of Boston University, Boston, MA (US)

( * ) Notice: Subject to any disclaimer, the term of this patent is extended or adjusted under 35 U.S.C. 154(b) by 0 days.

(21) Appl. No.: 10/377,178

(22) Filed: Mar. 1, 2003

(65) Prior Publication Data

US 2004/0168982 A1 Sep. 2, 2004

(51) Int. Cl.
*G01N 35/08* (2006.01)
*G01N 21/00* (2006.01)
*B01D 61/00* (2006.01)
*G01N 35/00* (2006.01)

(52) U.S. Cl. .................... 210/321.6; 210/649; 210/645; 210/498; 210/500.26; 436/180; 436/54; 436/43; 422/59; 422/63

(58) Field of Classification Search ....................... None
See application file for complete search history.

(56) References Cited

U.S. PATENT DOCUMENTS

| | | | | |
|---|---|---|---|---|
| 5,783,148 | A | 7/1998 | Cottingham et al. | 422/56 |
| 5,972,710 | A * | 10/1999 | Weigl et al. | 436/34 |
| 6,368,871 | B1 * | 4/2002 | Christel et al. | 436/180 |
| 2002/0086329 | A1 * | 7/2002 | Shvets et al. | 435/7.1 |
| 2002/0182241 | A1 | 12/2002 | Borenstein et al. | 424/422 |
| 2003/0003575 | A1 | 1/2003 | Vacanti et al. | 435/371 |

OTHER PUBLICATIONS

Kaihara et al., "*Silicon Micomachining to Tissue Engineer Branched Vascular Channels for Liver Fabrication*", Tissue Engineering, p. 105-117, vol. 6, No. 2, 2000.
Borenstein et al., "*Microfabrication Technology for Vascularized Tissue Engineering*", Kluwer Academic Publishers, 4:3, p. 167-175, 2002.
Anderson et al. "*Microfabrication and Microgluidies for Tissue Enginnering: State of the art and Future Opportunities*" The Royal Society of Chemistry, p. 98-103, 2004.
Tracey et al., "*A Silicon Micromachined Device for Use in Blood Cell Deformability Studies*", IEEE Transactions on Biomedical Engineering, vol. 42, No. 8, p. 751-761, 1995.
Tsukada et al., "*direct Measurement of Erythrocyte Deformability in Diabetes Mellitus with a Transparent Micochannel Capillary Model and High-Speed Video Camera System*", Academic Press, vol. 61, p. 231-239, 2001.
Frame et al., "*A System for Culture of Endothelial Cells in 20-20-μm Branching Tubes*", Microcirculation, vol. 2, No. 4, p. 377-385, 1995.
Kikuchi et al., "*Modified Cell-Flow Microchannels in a Single-Crystal Silicon Substrate and Flow Behavior of Blood Cell*", Microvascular Research, vol. 47, p. 126-139, 1994.

(Continued)

*Primary Examiner*—Krishnan S Menon
(74) *Attorney, Agent, or Firm*—Ohlandt, Greeley, Ruggiero & Perle, L.L.P

(57) ABSTRACT

A microvascular network device comprising: a substrate; at least one microchannel; at least one opening to the microchannel for sample entry; at least one opening to the microchannel for sample exit; and an aspirator which causes the sample to traverse the microchannel.

16 Claims, 3 Drawing Sheets

OTHER PUBLICATIONS

Cokelet et al., "*Fabrication of in Vitro Microvascular Blood Flow Systems by Photolithography*", Microvascular Research, vol. 46, p. 394-400, 1993.

Wilding et al., "*Manipulation and Flow of Biological fluids in Straight Channels Micomachined in Silicon*", Clinical Chemistry, vol. 40, No. 1, p. 43-47, 1994.

Sutton et al., "Technical Report: *A Novel instrument for Studying the Flow Behaviour of Erythrocytes Through Micochannels Simulating Human Blood Capillaries*", Microvascular Research, vol. 53, p. 272-281, 1997.

Pries et al., "*Biophysical Aspects of Blood Flow in the Microvasculature*", Elsevier, Cardiovascular Research, vol. 32, p. 654-667, 1996.

T. M. Griffith, "*Temporal Chaos in the Microcirculation*", Elsevier, Cardiovascular Research, vol. 31, p. 342-358, 1996.

Kiani et al., "*Fluctuations in Microvascular Blood flow Parameters Caused by Hemodynamic Mechanisms*", the American Physiological Society, p. H1822-H1828, 1994.

Johnson et al., "*Regulation of Blood Flow in Single Capillaries*", Dept of Physiology, Indiana University School of Medicine, p. 1405-1415.

Barclay et al., "*A Method for Detecting Chaos in Canine Myocardial Microcirculatory Red Cell Flux*", Microcirculation, Nature America Inc., vol. 7, p. 335-346, 2000.

Carr et al., "*Nonlinear Dynamics of Microvascular Blood Flow*", Medical Engineering Society, vol. 28, p. 641-652, 2000.

"*Deformation of Red Blood Cell in Capillaries*", p. 717-719, May 9, 1969.

Sambuceti et al., "Special Medical Editorial: *Why Should we Study the Coronary Microcirculation?*", the American Physiological Society, p. H2581-H2584, 2000.

Fung et al., "*High-Resolution Data on the Geometry of Red Blood Cells*", Biorheology, vol. 18, p. 369-385, 1981.

Barbee et al., "*The Fahraeus Effect*" Microvascular Research, vol. 3, p. 6-16, 1971.

Fahraeus et al., "*The Viscosity of the Blood in Narrow Caplillary Tubes*", the Pathological Institute, p. 562-568, Dec. 6, 1930.

August Krogh, "*Studies on the Physiology of Capillaries*", the Laboratory of Zoophysiology, Copenhagen University, p. 413-421.

McDonald et al., "*Poly(dimethylsiloxane) as a Material for Fabricating Microfluidic Devices*", Accounts of Chemical Research, American Chemical Society, vol. 35, No. 7, p. 491-499, Jul. 2002.

Whitesides et al., "*Components for Integrated Poly(dimethylsiloxane) Microfluidic Systems*", Wiley-VCH Verlag GnbH & Co.KgaA, Weinheim, vol. 23, p. 3461-3473, 2002.

Jo et al., "*Surface Modification Using Silanated Poly(ethylene glycol)s*", Elsevier, vol. 21, p. 605-616, 2000.

Alcantar et al., "*Polyethylene Glycol-coated Biocompatible Surfaces*", John Wiley & Sons, Inc., 2000.

Deible, "*Molecular Barriers to Biomaterial Thrombosis by Modification of Surface Proteins with Polyethylene Glycol*", Elsevier, vol. 19, p. 1885-1893, 1998.

Zhang et al., "*Modification of Si(100) Suface by the Grafting of Poly(ethylen Glycol for Reduction in Protein Adsorption and Platelet Adhesion*", John Wiley & Sons,. Inc., 2001.

Wu et al., "*Polymer Microchips Bonded by $O_2$ Plasma Activation*", vol. 23, p. 782-790, 2002.

\* cited by examiner

MICROVASCULAR NETWORK DEVICE

FIELD OF THE INVENTION

The present invention relates to microvascular devices. More particularly, the present invention relates to micro-scale devices that simulate the capillary networks and their physiological function. Still more particularly, the devices of the invention preferably provide simulated actual capillary networks with respect to scale and function and degree of connectivity for both in vitro blood diagnostic assessments and basic studies of the microvessels.

DESCRIPTION OF THE PRIOR ART

Oxygen and nutrient delivery, as well as waste removal, are determined by blood flow in richly branching capillary networks. These networks are fed by the smallest arterial branches (precapillary arterioles) and emptied by the smallest venous subdivisions (postcapillary venules). Normal red blood cells (RBC) have an average diameter of 7.6 µm (Fung, 1981). Capillaries can have diameters as small as 4 µm (Milnor, 1990). Therefore, RBC must deform to pass through, as well as enter, capillary microchannels. This process of RBC deformation and elongation is thought to facilitate gas transfer by increasing the surface contact area between RBC and capillary endothelium. Local blood flow is vitally important for the subset of cells living in the diffusion-limited supply domain of any given capillary network. Obstruction or reduction of microcirculatory blood flow can lead to catastrophic consequences for the affected cells or tissues and even for the whole organism if the obstruction impairs or diminishes the function of a vital organ (Sambuceti et al., 2000).

The flow of blood in actual microvascular networks has been found to exhibit chaotic temporal oscillations (Griffith, 1996). Kiani et al. proposed that such oscillations may occur in the absence of biological regulation and could result entirely from specific nonlinear rheological properties of blood within microvascular networks (Kiani et al., 1994). It has been proposed that both the Fahraeus-Lindqvist effect (Fahraeus and Lindqvist, 1931) and plasma skimming (Krogh, 1921) are essential for chaotic microvascular flow dynamics (Carr and Lacoin, 2000). Direct validation of these computational results using in vivo experiments may be prohibitively complex or even impossible. It would be a Herculean task to measure and control all of the relevant variables and simultaneously prevent the intrusion of compensatory physiological responses. Thus, an in vitro model of microvascular networks is essential for critical evaluation and/or validation of existing theory, models and computer simulations.

Cokelet et al. described a simple modification of standard photolithography that was used to fabricate systems of interconnected microchannels (Cokelet et al., 1993). This and other methods have been successfully adapted for production of flow systems that are used for endothelial cell culture (Frame and Sarelius, 1995; Borenstein et al., 2002).

Current instrumentation does not provide means to obtain actual information regarding the flow of blood in capillary network channels. There, in fact, is a need to obtain information regarding the flow of blood through capillary networks. Also, there is a need for a system to sort, separate, or otherwise distinguish the flow of cells, including, but not limited to, microorganisms and blood cells.

The present inventors have uniquely developed a device for which is capable of evaluating the flow of a slurry of the formed elements (to include red and white cell, platelets as well as other formed elements), as well as the suspending liquid solution of proteins and salts, through a capillary network.

These and other objects and advantages of the present invention and equivalents thereof, are achieved by the methods and devices of the present invention described herein and manifest in the appended claims.

SUMMARY OF THE INVENTION

A device having microchannels arranged in a network design to resemble those actually encountered in the circulation of various humans and animal model systems. A multivascular network device and method of manufacture. The device preferably comprises microchannels of elastomeric material providing for entry and exit of liquid samples of cells, preferably blood cells, and flow of such cell samples through microchannels of the device. The device is useful for the separation of cells and the in vitro evaluation of flow of liquid samples of cells, preferably blood cells. The device is especially useful for evaluating transport functions in capillary networks that comprise a variety of formed elements varying in number and composition and suspended in a variety of solutions varying in protein concentration with special emphasis on network robustness, i.e., the capacity of such networks to accommodate and contain without deterioration of transport function varying amounts of red cells and white cells.

A device having a synthetic, preferably transparent and preferably built on the actual scale of human capillaries, microvascular network, which is capable of evaluating the flow of a slurry of the formed elements (to include red and white cell, platelets as well as other formed elements), as well as the suspending liquid solution of proteins and salts, through a capillary network.

The device is preferably for simulation of the flow of blood cells through a capillary network.

The present invention also include a method of manufacturing this unique microvascular network device.

The present inventors have uniquely discovered that the use of fabrication technology to manufacture devices having a 2D network of microchannels in transparent silicone elastomer work particularly well in making such microvascular network devices. These devices provide certain characteristic patterns of physiological blood flow in living microvascular networks. Uses of the invention are also provided.

This unique microvascular network device comprises: a substrate; at least one microchannel comprised of elastomeric material; at least one opening to the microchannel for sample entry; at least one opening to the microchannel for sample exit; and aspiration pressure means for providing movement of liquid sample through the at least one microchannel. The substrate of the microvascular network device is comprised of glasses, plastics, polymers, metals, ceramics, organic materials, inorganic materials, and any combinations thereof. A preferred substrate is transparent and readily uses the microchannel formation. The device preferably has a plurality of microchannels each having a diameter or width (and as well a depth) from about 1 µm to about 100 µm.

Microchannels can be variable in cross section which can be rectangular circular or any similar shape. Samples for use in the device may be selected from the group consisting of: cells, microorganisms, and any combinations thereof. Preferred samples are whole blood, white blood cells, and most preferably red blood cells and platelets. The device of the invention preferably has a network of microchannels which may be homogeneous or heterogeneous in size. A preferred elastomeric material is silicone elastomer.

The present invention also provides a method of producing a microvascular network device comprising: applying onto a first substrate an energy sensitive composition to produce an energy sensitive coating; patternwise exposing the energy sensitive coating with an energy source to produce a coating having exposed and unexposed regions; contacting a developer and the coating having exposed and unexposed regions to selectively remove the exposed regions to produce a patterned layer; curing the patterned layer; etching the patterned layer and removing the excess energy sensitive coating to produce a patterned substrate; providing transparent liquid elastomer to the patterned substrate and thereafter baking the patterned substrate to produce a molded microchannel cast structure; removing the molded microchannel cast structure from the substrate; capping the molded microchannel cast structure with an elastomer-coated second substrate thereby sealing the microchannels of the microchannel cast structure thereby providing a microvascular network device. The first substrate is preferably silicon and the second substrate is transparent and preferably glass or a functional equivalent. The energy sensitive coating is preferably a positive resist known in the art. The preferred energy source of the manufacturing method is an electron beam, but alternative energy sources and lithographic methods may be used. A preferred elastomer is silicone elastomer.

However, neither the invention substrate nor the microchannel material is limited to any specific material, but may use any material that satisfies the structural and functional requirements of the invention. For example, any material that can be cast into microchannel networks may be employed. A wide spectrum of materials can be used for channel castings. The microchannel material is preferably not hostile to blood cells, especially red blood cells, and may optionally bind lubricant material that may be useful to facilitate cell movement. For example, PEG, sialynated PEG, and the like may be used to coat microchannels.

Also provided is a method for separating blood cells or evaluating the flow of blood cells in vitro comprising: flowing a liquid sample medium selected from the group of: whole blood, red blood cells, white blood cells, we note that the device is also suitable for the study of all of the above named formed elements in normal as well as pathological states, that is, red cell that are more rigid because of diabetes mellitus, red cells that are infected with parasitic forms as occur in malaria, red cells that demonstrate genetic abnormalities, such as those found in thalasemia and sickle cell decease, i.e., not only limited to the normal formed elements, but as well to cells of which display the changes of metabolic or parasitic deceases and other pathological processes that involve the formed elements and any combinations thereof, through a microvascular network device.

The microvascular network device comprises: a substrate; at least one microchannel comprised of elastomeric material; at least one opening to the microchannel for sample entry; at least one opening to the microchannel for sample exit; and aspiration pressure means for providing movement of liquid sample through the at least one microchannel.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patents, and other references mentioned herein are incorporated by reference in their entirety. In case of conflict, the present specification, including definitions, will control. In addition, the materials methods, and examples are illustrative only and not intended to be limiting of the invention Other features and advantages of the invention will be apparent from the following detailed description, and from the claims.

BRIEF DESCRIPTION OF THE DRAWINGS

FIG. 2A shows red blood cells deformed into parachute-like shapes; FIG. 2B shows red blood cells in bullet-like shapes; and FIG. 2C show rouleaux formation which are composed of column formations of red blood cells most usually encountered in microchannel, but also encountered in larger channels as well.

DETAILED DESCRIPTION OF THE INVENTION

Figure 1:
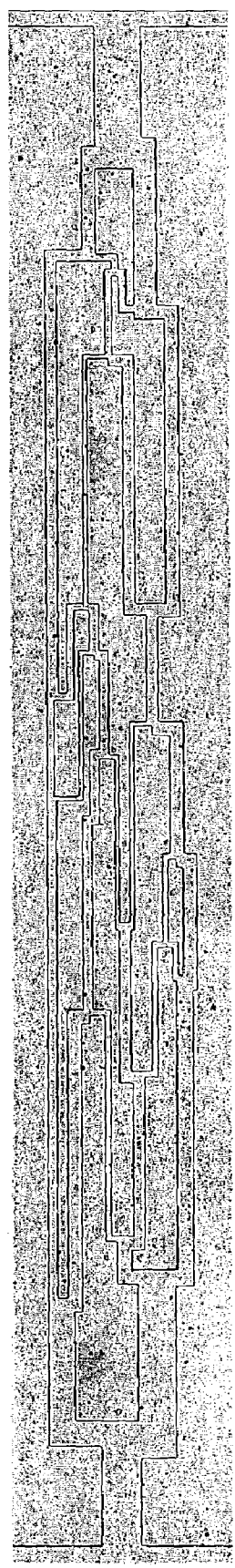
FIG. 1 shows an illustration of a network unit.

Mold fabrication. The network 2D pattern was drawn with L-Edit (Tanner FDA, Tanner Research, Inc.) and converted into a machine specific format using CATS (Transcription Enterprises). The silicon wafer (4", 475-575 μm, 1-20-cm, <1-0-0>; Silicon Quest International) was cleaned in oxygen plasma (1 min, 1000 W; Branson/IPC P2000 Barrel Etcher), dehydrated on a hot plate (5 min, 170° C.), spin-coated with positive resist (XP 9947) and baked (3 min, I 35° C.). Direct e-beam writing was used to transfer the pattern onto the wafer (EBMF-10.5/CS, Cambridge Instruments). After post-exposure baking (90 sec, 135° C.) and developing (1 min, 300 MOF), the wafer was cleansed in oxygen plasma (30 sec, 100 W). The pattern was etched using the Bosch fluorine process (Unaxis SLR 770 ICP Deep Silicon Etcher) and residual resist was stripped to bare silicon with oxygen plasma (10 min, 1000 W; Branson/IPC P2000 Barrel Etcher). The silicon wafer was subsequently used as a negative mold.

Casting. Casts of the microvascular network were obtained by pouring transparent liquid elastomer (RTV 615 A/B; G.E. Silicones) onto the wafer, baking it (1 hr, 100° C.), peeling the cast off the wafer and cutting it to size. A glass slide which contains an opening (approximately 2 mm for the purpose of establishing flow ) has been placed or drilled. (Micro Slides, VWR Scientific) was spin-coated with the same elastomer and used to seal the microchannels. The cast microchannels and elastomer covered glass slide were cleaned with oxygen plasma (100 sec; Plasma Cleaner/Sterilizer, Harrick Scientific Corporation) and the microchannels sealed by apposition of the glass slide without compressive force. Microchannels were flushed with 1% PEG-silane (O-Methyl-O'-[2-(trimethoxysilyl)ethyl]polyethylene glycol, MW 5000, Shearwater Polymers, Inc.) for 20 minutes, followed by perfusion with GASP buffer (see below) for 5 minutes prior to use.

Fluidics. A simple aspiration system was used to sustain flow inside the microchannels. One end of the array was cut to provide an opening for sample entry, and the other end was situated on the glass slide above a predrilled 2 mm hole. The hole was connected through continuous plastic tubing (I.D.=2 mm) to a reservoir (25 mm in diameter), which served as a receptacle for collecting waste buffer. Adjustment of the height difference between the entry into the microchannels and the liquid meniscus in the reservoir provided accurate adjustment of the aspiration pressure within the system. A wide reservoir was chosen to insure that pressure was virtually constant during each experiment.

Imaging. The image acquisition system consisted of an Olympus BX51 microscope with an attached high-speed digital CMOS camera (Silicon Video 2112; Epix, Inc.) and a frame grabber board (PIXCI D2X; Epix, Inc.) mounted in a dedicated PC (Dimension XPS D300, Dell). Frame sequences were captured in computer memory and saved on hard drive (XCAP-Lite; Epix, Inc.) for analysis using custom software written in MATLAB (Mathworks, Inc.) or in C++ (Microsoft Visual C++ 6.0; Microsoft, Corp.).

Sample preparation. Blood was collected by venipuncture (from healthy informed consenting volunteers) into a heparinized plastic syringe (Becton Dickinson). RBC were washed three times in phosphate buffered saline (PBS) to reduce the concentration of white blood cells (WBC) and platelets below $2\times10^3/\mu l$ and $3\times10^3/\mu l$ respectively. Washed cells were diluted into GASP buffer containing 9 mM $Na_2HPO_4$, 1.3 mM $NaH_2PO_4$, 140 mM NaCl, 5.5 mM glucose, and 1% bovine serum albumin, pH 7.4, osmolarity 290 mmol/kg. The hematocrit of RBC in GASP was quite variable, sample size was 20 µl and experiments were performed at room temperature. This is not to exclude the possibility of different sample sizes and running at different temperatures as well.

Chemicals. Chemicals were either purchased from Sigma (with the exceptions mentioned above) or supplied by the Cornell Nanofabrication Facility.

Network parameters. The prototype, or the specimen, or embodiment illustrated in FIG. 1 consists of microchannels that range in width from 6 to 63 µm with a depth of 5.4 µm throughout. A manufactured embodiment of the invention contains fifteen network units arranged in parallel and served by a distribution array upstream and an exit array downstream. With reference to FIG. 1, each network unit consists of 34 microchannels of widths ranging from 6 to 63 µm. However, the microchannels of such devices can have a diameter or width from about 1 µm to about 100 µm and a similar variability in depth. Channel depth of one embodiment was 5.4 µm throughout, but any convenient or approximate channel depth may be employed.

Pressurized Sample Flow. Under an aspiration pressure of 20 cm of $H_2O$ the combined flow rate through a sample network is about 0.5 nl/s. The meniscus rises about 1 nm/s in the waste-collecting reservoir and falls by ~20 nm/s at the entry port, thereby changing the operative driving pressure by only 21 nm $H_2O$/s. An aspiration pressure of about 20 cm $H_2O$ is thus taken as the operating pressure throughout an experiment. The movement of liquid sample may conveniently be varied by altering aspiration pressure.

Figure 2:
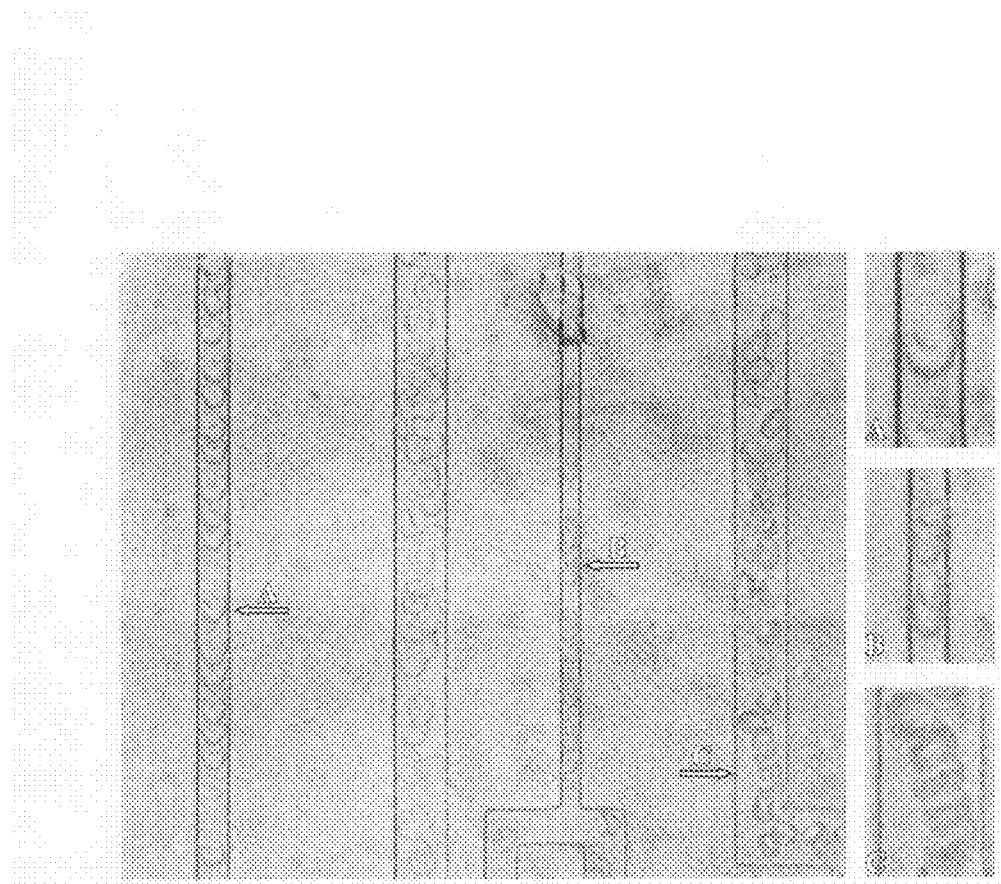
FIG. 2 shows a top view of red blood cells within the microchannels in a prototype microvascular device.

RBC morphology. Cast silicone rubber microchannels are rectangular in cross-section and thus very different from actual microvessels. In spite of this clear difference, there was a striking similarity between the shapes of RBCs in capillaries of our model microvascular network (FIG. 2) and in the actual mammalian microcirculation in vivo (see for example Fung, 1993 and Branemark, 1971). One can readily observe RBC deformed into parachutes (FIG. 2,A) or bullet-like shapes (FIG. 2, B) traveling single file in microchannels of 10 and 6 µm wide respectively. One can also observe occasional rouleaux (FIG. 2, C), which would likely be more frequently observed if protein concentrations in the perfusion fluid were closer to the physiological composition.

Figure 3:
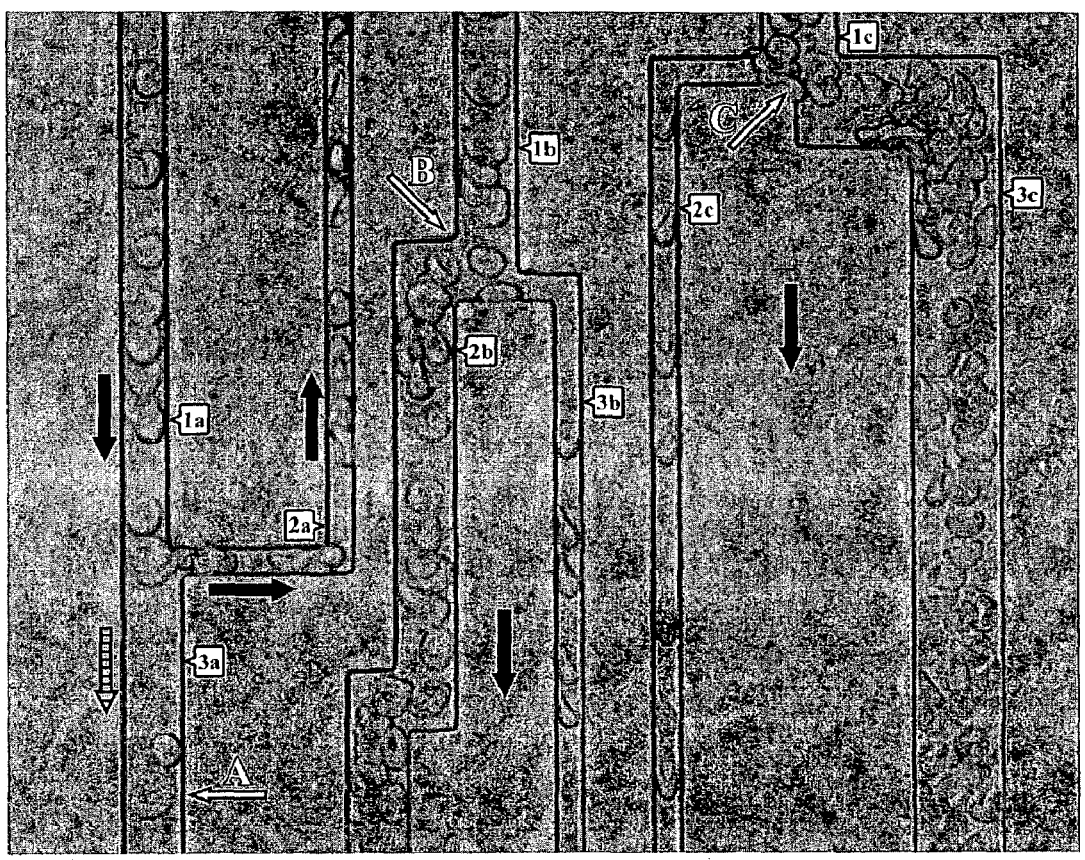
FIG. 3 shows flow patterns of blood cells in microchannels of a microvascular device; "A" indicates a white blood cell adhering to the microchannel wall; and as a consequence, blocking flow in that channel. "B" and "C" show plasma skimming or unequal distribution of red blood cells at bifurcation sites in microchannels of a microvascular device.

Flow patterns. Collateral flow pathways are an essential feature for robust vascular network function in vivo. Activated WBC or small cellular aggregates can clog microvessels and significantly retard local blood flow (Fung, 1993). In such cases, blood flow in adjacent vessels will often reverse direction to maintain perfusion levels. We also observe similar flow reversal in our microchannel network when a WBC adheres to the microchannel wall (FIG. 3, A).

Plasma skimming is a well-documented feature of the mammalian microcirculation, and results in an unequal distribution of RBC at bifurcation sites in microvascular networks (Fung, 1993). In computer simulations plasma skimming has been found essential for the appearance of nonlinear oscillations in microvascular flow (Carr and Lacoin, 2000). Plasma skimming is readily observed in the device of the present invention (c.f., FIGS. 3, B and C).

Modifications. Many of the design features of the prototype may conveniently be modified or optimized. For example, right angle geometry in prototype bifurcations may interfere with the smooth entry of cells into daughter branches and should be adjusted to achieve streamlined flow. An alternative arrangement of channel morphology has been fabricated in a more recent embodiment of the invention in which the branching angles approach more closely what would be expected in an actual physiological capillary network. Accurate control and monitoring of pressure and flow are essential for the development of quantitative descriptions of the Fahraeus-Lindqvist effect and plasma skimming in next generation systems intended for use in quantitative modeling. Microvascular cassette ports for drug injection capabilities as well as more precise sample handling as well as to the incorporation of valves for the regulation or switching or flow and as well sensors for the measurement of pressure, flow and potentially the tension of oxygen or other gases and or ions such as $Ca^{++}$ would further increase the analytical power and widen the spectrum of possible instrument applications.

Various embodiments of the invention, including sizes and shape of microchannels, may be employed. Some embodiments may be suitable for some applications, but would have fundamental constrains with other applications. For example, a manufacturing technique used here produces essentially two-dimensional patterns of microvascular networks. In this embodiment, all microchannels of the network now have the same depth, which inevitably leads to the use of some rather wide microchannels in our simulated feeding arterioles and collecting venules. We suggest, however, that the former limitation of the technique introduces a benign simplification of the microvascular network design, allowing for more precise manufacturing, reliable imaging and data analyses based on very obliging channel geometry. Multistage successive etching of deeper channels should address the latter limitation.

Uses. It is extremely difficult to design, control and reproduce microvascular network experiments in vivo (Fung, 1997). Experiments with models allow precise control over experimental variables and accurate quantification of results. The prodigious 'room-size' experimental models designed according to the principles of kinematic and dynamic similarity have also provided valuable insights (see for example Yen and Fung, 1978). These model systems are, however, compelled to take rather striking liberties with some of the intrinsic features and properties of actual network systems. One conspicuous problem is that it would seem virtually impossible to construct giant RBC and WBC with authentic rheological properties in such non-dimensionalized model systems. These oversized models are also impaired by the absence of regulatory mechanisms that depend upon intrinsic RBC molecular signal transduction systems. In addition, the cell-to-cell interactions, which undoubtedly have a significant impact on actual microcirculatory dynamics, are also absent in the room sized models. These important experimental problems have strengthened our resolve to develop in vitro scale-to-scale models of actual microvascular networks in which one can effectively study the behavior of fully functional red and white cells under controlled circulatory conditions The prototype model system has applications in a variety of microvascular network studies. This would include studies on the robustness of network function in the presence of elevated white cell counts or cellular aggregates. The former is a physiological response to bacterial infection or a pathological manifestation of neoplastic transformation of leukocyte precursors. The latter occurs in association with diabetes or other hypercoagulable states and may cause or accompany vascular occlusions that can damage heart or brain tissues. Using available pattern generation capabilities, a range of microvascular network designs and complexities can be studied. Computer simulations have shown that plasma skimming and the Fahraeus-Lindqvist effect might entirely account for nonlinear temporal oscillations in microvascular blood flow in the absence of biological regulation. This question can be directly studied and simulated with the device of the invention. Some microvascular regulatory agents, such as NO, have documented effects on red cell deformability which could effect microvascular flow dynamics and even serve as an independent mechanism for its regulation. The nonlinear dynamics of local blood flow and its dynamic regulation at the local level are also directly studied and simulated with the device of the invention. By modifying the device to include a drug injection port, more precise measurements of dose response relationships and latencies for the effects of such regulatory agents on RBC properties and behaviors in microvascular networks can be obtained. The present invention is also a useful validation tool for earlier computer simulations and theoretical models.

The present microvascular network device may conveniently be used for cell sorting applications, preferably red blood cell sorting. For example in one embodiment this is achieved by arranging capillary networks and larger channels in repeating sequence. This would literally distinguish those red cells with greater deformability which thereby move more rapidly through the network and those with the least deformability which would move more slowly. This would actually provide in a microvascular flow context the most relevant and direct measurement of the ability of cells to move in small channel that has ever been made. We could also sort cells on the basis of other physical and chemical parameters. For example, selection of microchannels of a certain size, varying operating pressure, varying sample fluids, varying temperature, varying pH, osmolality, viscosity etc. The device of the invention is particularly useful for sorting red blood cells, including, but not limited to, separation of white blood cells from red blood cells (including, for example, red blood cells that are physiologically aged, morphologically compromised etc.), platelets, and the like. The channels might be surface-treated with material(s) having affinity for certain cells by use of antibodies or other chemical means of selection. The process of removing or sorting aged or otherwise qualitatively compromised red blood cells that are undesirably for stored blood or blood transfusion is referred to as editing. This is a preferred application.

Although the present invention describes in detail certain embodiments, it is understood that variations and modifications exist known to those skilled in the art that are within the invention. Accordingly, the present invention is intended to encompass all such alternatives, modifications and variations that are within the scope of the invention as set forth in the following claims.

What is claimed is:

1. A microvascular network device for a biological sample comprising:
    a substrate;
    at least one network unit disposed in said substrate; said at least one network unit consisting of a single entry and a single exit for the sample, said at least one network unit also comprising a plurality of microchannels; wherein each of said microchannels being either i) a microchannel that branches into two daughter microchannels, or ii) a convergence of two microchannels; wherein said plurality of microchannels receives the sample from said single entry and drains the sample into said single exit; and
    an aspiration pressure means for providing movement of liquid sample through said at least one network unit.

2. The device of claim 1, wherein said substrate and said at least one network unit are both formed of at least one material selected from the group consisting of: glass, plastic, polymers, metal, ceramic, organic materials, inorganic materials, and any combinations thereof.

3. The device of claim 1, wherein said substrate is glass.

4. The device of claim 1, wherein each of said plurality of microchannels has a diameter or width in the range between about 6 μm to about 63 μm.

5. The device of claim 1, wherein the sample is selected from the group consisting of: cells, microorganisms, and any combinations thereof.

6. The device of claim 1, wherein the sample is whole blood.

7. The device of claim 1, wherein the sample red blood cells.

8. The device of claim 1, wherein said plurality of microchannels are a plurality of dimensionally homogenous microchannels.

9. The device of claim 1, wherein said plurality of microchannels are a plurality of dimensionally hetrogenous microchannels.

10. The device of claim 1, wherein said at least one network unit is formed of a silicone elastomer material.

11. The device of claim 1, wherein said at least one network unit is coated to facilitate sample movement.

12. A method for separating a liquid sample medium or evaluating the flow of a liquid sample medium in vitro comprising:
    flowing a liquid sample medium selected from the group consisting of whole blood, red blood cells, white blood cells, and any combinations thereof, through a microvascular network device wherein said microvascular network device comprises:
    a substrate;
    at least one network unit disposed in said substrate; said at least one network unit consisting of a single entry and a single exit for the sample, said at least one network unit also comprising a plurality of microchannels; wherein each of said microchannels being either i) a microchannel that branches into two daughter microchannels, or ii) a convergence of two microchannels; wherein said plurality of microchannels receives the sample from said single entry and drains the sample into said single exit; and an aspiration pressure means for providing movement of sample through said at least one network.

13. The method of claim 12, wherein said plurality of microchannels are selected from the group consisting of: homogeneous microchannels and heterogeneous microchannels.

14. The method of claim 12, wherein said each of said plurality of microchannels has a diameter and a width in the range between about 6 μm to about 63.

15. A microvascular network device for a biological liquid sample medium comprising:
 a substrate;
 a plurality of network units;
 each of said plurality of network units consisting of a single entry and a single exit for the sample, said network unit also comprising a plurality of microchannels; wherein each of said plurality of microchannels being either i) a microchannel that branches into two daughter microchannels , or ii) a convergence of two microchannels; wherein said plurality of microchannels receives the sample from said single entry and drains the sample into said single exit;
 an aspiration pressure means which causes said liquid sample medium to traverse each of said plurality of network units.

16. The device of claims 1 or 15, wherein said each of said plurality of microchannels has a depth of 5.4 μm.

* * * * *